United States Patent
Kawakami et al.

[11] Patent Number: 5,728,583
[45] Date of Patent: Mar. 17, 1998

[54] DETERMINATION OF ABNORMAL PART OF BLOOD FUNCTIONS

[75] Inventors: Keiko Kawakami, Kawasaki; Yoshiyuki Harada, Futtsu; Tadashi Sakon; Yutaka Kishida, both of Kawasaki; Yasuo Ikeda, Tokyo, all of Japan

[73] Assignee: Jeol, Ltd., Akishima, Japan

[21] Appl. No.: 759,205

[22] Filed: Dec. 4, 1996

Related U.S. Application Data

[63] Continuation of Ser. No. 337,695, Nov. 10, 1994, abandoned.

[30] Foreign Application Priority Data

Nov. 11, 1993 [JP] Japan .................. 5-282597
Sep. 9, 1994 [JP] Japan .................. 6-215883

[51] Int. Cl.$^6$ .................................. G01N 33/86
[52] U.S. Cl. .................. 436/69; 436/86; 436/52; 422/73; 422/81; 422/82.01; 422/82.02; 435/2; 435/13; 310/311; 310/312
[58] Field of Search .................. 436/63, 69, 86, 436/52; 422/73, 81, 82.01, 82.02; 435/2, 13, 287.9; 310/311, 312

[56] References Cited

U.S. PATENT DOCUMENTS

| | | | |
|---|---|---|---|
| 4,236,893 | 12/1980 | Rice | 436/513 |
| 4,242,096 | 12/1980 | Oliveira et al. | 436/500 |
| 4,246,344 | 1/1981 | Silver, III | 435/39 |
| 4,735,906 | 4/1988 | Bastiaans | 436/527 |
| 4,789,804 | 12/1988 | Karube et al. | 310/311 |
| 5,001,053 | 3/1991 | Takahashi et al. | 435/7.1 |
| 5,211,054 | 5/1993 | Muramatsu et al. | 73/64.42 |
| 5,306,644 | 4/1994 | Myerholtz et al. | 436/149 |

OTHER PUBLICATIONS

Matsuda et al. *ASAIO Journal*, Jul.–Sep. 1992, pp. M171–M173.
Muramatsu et al. *Biosensors & Bioelectronics*, vol. 6, 1991, pp. 353–358.
Abstract–JP4–32767, Miya et al., Feb. 4, 1992, accession #116: 231 312 CA.
Sakariassen et al. *Journal of Laboratory & Clinical Medicine*, vol. 102, No. 4, Oct. 1983, pp. 522–535.
Misselwitz et al. *Thrombosis Research*, vol. 48, No. 5, 1987, pp. 597–602.
Kawakami et al. *ASAIO Journal*, Jul.–Sep. 1993, pp. M558–M560.
Fressinaud et al. *Blood*, vol. 80, No. 4, Aug. 15, 1992, pp. 988–994.
Folie et al. *Blood*, vol. 72, No. 4, Oct., 1988, pp. 1393–1400.

*Primary Examiner*—Maureen M. Wallenhorst
*Attorney, Agent, or Firm*—Kenyon & Kenyon

[57] ABSTRACT

A method and apparatus for determining an abnormal component of blood functions is described. A whole blood sample is cycled as a laminar flow through a flow cell having a measuring element prepared by plating the surface of a plate-shaped quartz oscillator with a protein layer. The amount of adhesion of the blood component on the protein layer is determined on the basis of the change in resonance frequency of the measuring element. The measured value is compared with a standard value of adhesion for blood from a healthy individual.

11 Claims, 10 Drawing Sheets

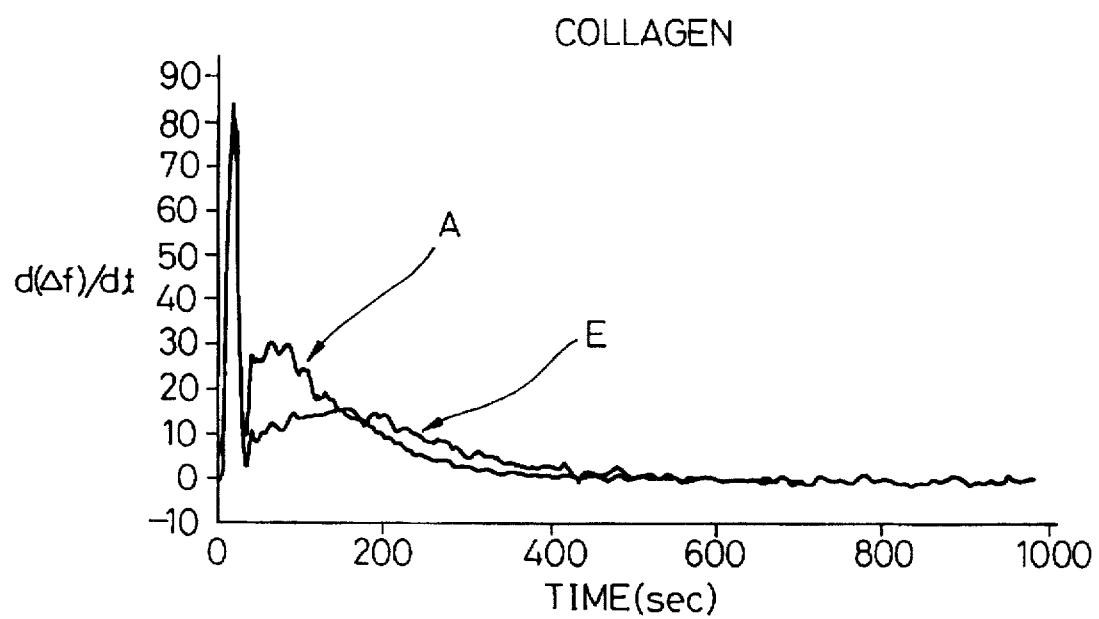

5,728,583

DETERMINATION OF ABNORMAL PART OF BLOOD FUNCTIONS

This application is a continuation of application Ser. No. 08/337,695, filed on Nov. 10, 1994 now abandoned.

BACKGROUND OF INVENTION

1. Field of Invention

The present invention relates to a method and device for easily determining an abnormal part of blood functions.

The present invention further relates to a method for determining the thrombogenic effects of anticoagulants against thrombus adhesion to materials with high blood coagulating properties, for example medical tool materials such as artificial blood vessels and other artificial organs and medical tubes, or biological tissues such as blood vessels.

2. Description of the Related Art

For the treatment of diseases due to blood dysfunctions such as bleeding tendency or thrombogenesis, it is important to know abnormal part of blood functions which causes the disease which displays such symptoms. Determination of blood dysfunction has customarily been made by aggregation reaction with platelets, one of the blood components, elicited with either a non-physiological drug or a drug in a non-physiological concentration, with the blood either stationary or in a turbulent state which cannot occur in the body.

The conventional determining methods are carried out under conditions which differ from the actual environment of the body, causing an inconvenience since the results of the determination have not always matched the clinical results. Furthermore, in platelet aggregation reactions, an abnormal part of blood functions is often not specifically defined, and in order to specifically determine an abnormal part of blood functions it is necessary to use very complicated and time consuming procedures wherein the cells are fractioned into proteins and various amounts thereof are measured, such as the Western blotting method. Consequently, the development has been sought of a method for determining an abnormal part of blood functions easily and under flow conditions similar to those in the body.

The determination of anticoagulant effects is extremely important in the development of a variety of medical materials, such as artificial blood vessels, used in the body, and in the development of drugs such as prophylactic and therapeutic agents for diseases related to blood coagulation. It has become particularly important to make such determination under the same flow conditions as in the body. In the past, these determining methods have been carried out by measurement of aggregation of platelets, one of the blood components, elicited with a drug either non-physiological or in an non-physiological concentration, with the blood either stationary or in a turbulent state which cannot occur in the body. Thus, since the conventional determining methods are carried out by measurement in an environment quite different from that of the body, the results of the determination have not always matched the clinical results. Therefore, the development has been sought of a simple method for determining blood coagulation properties of medicinal agents.

SUMMARY OF INVENTION

One of the objects of the present invention is to provide a method and a device for easily determining an abnormal part of blood functions under flow conditions very close to those in the body.

Another object of the present invention is to provide a simple method for determining the effects of anticoagulant agents under flow conditions close to those in the body.

BRIEF DESCRIPTION OF THE DRAWINGS

FIG. 14 is a differential waveform graph of FIG. 13.

[Explanation of Symbols]

Figure 1:
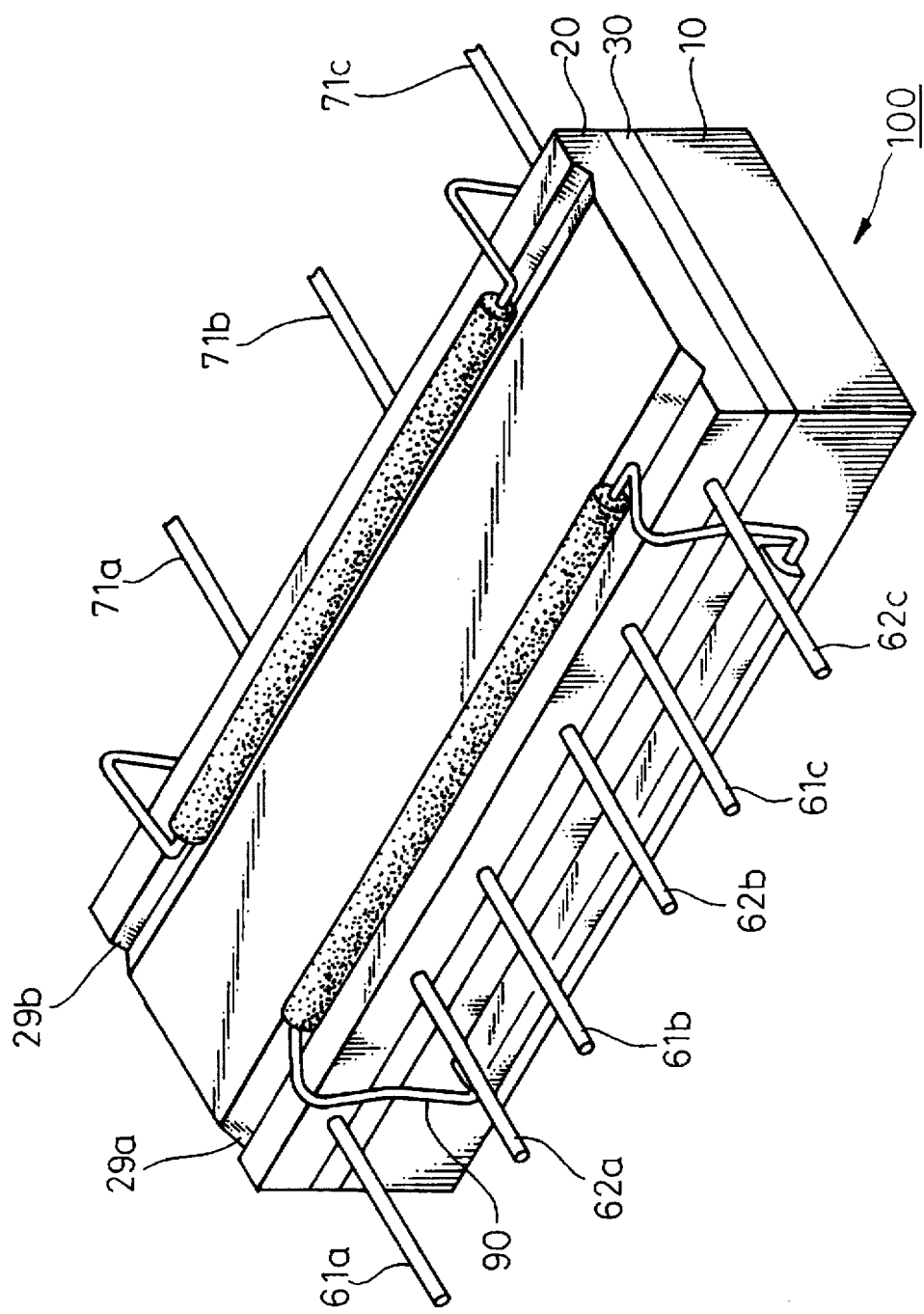
FIG. 1 is a perspective view of a flow cell.

10 lower member; 11a–11c pits; 20 upper member; 21a–21c collar-like raised sections; 22a–22c, 23a–23c holes; 24a–24c, 25a–25c slits; 30 outer seal member; 40a–40c cell compartment seal members; 50a–50c plate-shaped crystal oscillators; 51a–51c electrodes; 61a–61c, 62a–62c, 63, 64 tubes; 71a–71c cables; 72, 73 electrical contacts; 80 material layer; 82 underlying layer; 84 protein layer; 100 flow cell.

DETAILED DESCRIPTION OF THE INVENTION

According to the present invention, a measuring cell is prepared by fixing a protein layer onto the surface of a plate-shaped quartz oscillator. The measuring cell is incorporated in a flow cell, it is contacted with blood flowing in a laminar manner, and the change in the resonance frequency is measured, to determine the adhesion of the blood components on the protein layer. By comparing the adhesion of blood components measured on different protein layers, it is possible to determine an abnormal part of blood functions.

More specifically, the method for determining an abnormal part of blood functions according to the present invention is characterized by cycling a blood sample as a laminar flow in a flow cell which incorporates a measuring element prepared by coating the surface of a plate-shaped quartz oscillator with a protein layer; measuring the amount or rate of adhesion of the blood components on the protein layer based on the change in the resonance frequency of the measuring element; and comparing the measured value with a standard value corresponding to the amount of adhesion occurring when normal blood is cycled.

Instead of one measuring element there may be used a plurality of measuring elements coated with different proteins. The proteins may be human fibrinogen, human von Willebrand's factor, collagen, or the like.

The blood sample may be whole blood or component blood containing one or more blood cell components selected from erythrocytes, leukocytes and platelets.

Furthermore, the device for determining an abnormal part of blood functions according to the present invention is provided with a flow cell which incorporates a measuring element prepared by coating the surface of a plate-shaped quartz oscillator with a protein layer, means for flowing a blood sample through the flow cell, and means for measuring the change in the resonance frequency of the measuring element, and it may also be provided with means for comparing the value of the measured resonance frequency change with a prestored standard value, and means for outputting the results of the comparison. In addition, it may be provided with means for differentiating the signal of the measured resonance frequency change.

Another device for determining blood dysfunction sites according to the present invention is provided with a flow cell which incorporates a plurality of measuring elements prepared by coating the surface of plate-shaped quartz oscillators with different protein layers, means for flowing a blood sample through the flow cell, means for measuring the change in the resonance frequencies of the measuring elements, and means for comparing the values of the measured resonance frequencies with a standard value. The plurality of measuring elements may be a plate-shaped quartz oscillator coated with human fibrinogen, a plate-shaped crystal oscillator coated with human von Willebrand's factor and a plate-shaped crystal oscillator coated with collagen.

A plate-shaped quartz oscillator incorporated into the resonance circuit oscillates at a resonance frequency ($f_o$) perpendicular to the direction of its width. Here, if a weight ($\Delta W$) is incurred due to an adhesion layer caused by adhesion of blood substances onto the surface of the quartz oscillator, a change $\Delta f$ in the resonance frequency occurs such as described by the equation shown below. Thus, it is possible to calculate the weight $\Delta W$, i.e. the amount of adhesion from the resonance frequency change $\Delta f$.

$$\Delta f = f_o^2 \Delta W / NAp$$

where $\Delta W$=the change in mass, A=the area of the electrode, p=the specific gravity of the quartz, and N=the frequency constant of the quartz.

By forming various protein layers of collagen, fibrinogen, von Willebrand's factor, etc. on the surface of the quartz-oscillator, it is possible to compare the adhesion of the blood components onto each of these proteins and thereby determine an abnormal part of blood functions based on the results of the comparison.

As another embodiment of the present invention, the present invention provides a method for determining the anti-thrombogenic effects of experimental agents against thrombus formation caused by materials with high coagulating properties and biological tissue, characterized by forming a layer of a material with high coagulating properties or biological tissue on the surface of a crystal oscillator composing a portion of the wall of a flow cell, circulating blood containing the experimental agent through the flow cell, and detecting the adhesion of blood components on the layer of the material with high coagulating properties or biological tissue under the blood flow, based on the change in resonance frequency of the crystal oscillator.

According to the present invention, at least one portion of the wall of the flow cell consists of a crystal oscillator, a layer of a specific material with high coagulating properties or biological tissue is formed on the surface of the crystal oscillator, and blood is circulated through the flow cell to contact it with the layer of the material with high coagulating properties or biological tissue, thus causing coagulation of the blood and adhesion of the blood components onto the layer of the material with high coagulating properties or biological tissue. The result is measured as the change in the resonance frequency of the crystal oscillator. By comparing the change occurring when the agent-added blood is used with the change occurring when agent-free blood is used, it is possible both to determine whether or not the experimental agent has coagulating activity, and to measure the strength thereof in cases where the experimental agent has coagulating activity.

According to the method described above, it is possible to determine the anti-thrombogenic effects of experimental agents in the body by creating a flow rate of blood in the flow cell approximating the rate of blood flow in the body.

The method for determining anti-thrombogenic effects according to the present invention may be applied to a wide variety of anti-thrombogenic agents, and it may be used to evaluate the anti-thrombogenic effects of agents such as prostaglandin, which are already known to have an anti-thrombogenic effect against the blood coagulating activity of certain materials or biological tissues, or for screening of new anti-thrombogenic agents.

Regarding the flow cell composing the device used to carry out the method of the present invention, at least one portion of the wall thereof consists of a crystal oscillator, on the surface of which a layer of a material with strong coagulating properties or biological tissue may be formed so that the material or biological tissue is contacted with the blood circulating through the flow cell, and there are no particular restrictions on its concrete structure. As an example of such a flow cell there may be mentioned the flow cell described in the specification and drawings of Japanese Patent Application No. 4-319186.

The crystal oscillator used in the above-mentioned flow cell may be any commercially available one well-known to those in the field. Methods and devices for measuring resonance frequencies of crystal oscillators are also well-known to those in the field, and are commercially available.

The blood to be used in the method of the present invention may be of any type which causes a blood coagulation reaction in the presence of the above-mentioned material with strong blood coagulating properties or biological tissue, and it may be, for example, whole blood or blood from which a portion of the blood components of whole blood have been removed, such as component blood containing one or more blood components selected from erythrocytes, leukocytes and platelets. Methods of preparing component blood are well-known to those in the field.

As the material with strong blood coagulating properties to be attached to the surface of the crystal oscillator, there may be mentioned a variety of different medical materials, including artificial organs such as artificial blood vessels and artificial bones, and a variety of different medical tools such as tubes for dialysis and the like. The biological tissue may be from a blood vessel or the like.

In performing the method of the present invention, first component blood which causes no blood coagulation, for example component blood prepared by removing the leukocytes and platelets from heparinized blood, is circulated through the flow cell, stabilization to a constant temperature and for saturation of the amount of adhesion of protein in order to obtain a base line. It is known that saturation has been achieved when the resonance frequency of the crystal oscillator becomes constant. Next, blood containing the experimental agent is circulated through and the change in the resonance frequency of the crystal oscillator is measured. The change in the resonance frequency is measured in the same manner using blood containing none of the experimental agent.

The resonance frequency decreases as the amount of adhesion of protein to the crystal oscillator increases. Consequently, in cases where the decrease in the resonance frequency when using the agent-free blood is larger than when using the agent-containing blood, it is determined that the experimental agent has anticoagulant activity, i.e. an anti-thrombogenic effect.

By using component blood containing one of the components of whole blood, i.e. erythrocytes, leukocytes or platelets, the effect of each of the individual blood components on the anti-thrombogenicity may be determined.

EXAMPLES

The present invention is explained in detail below with reference to the drawings.

Example 1

Figure 2:
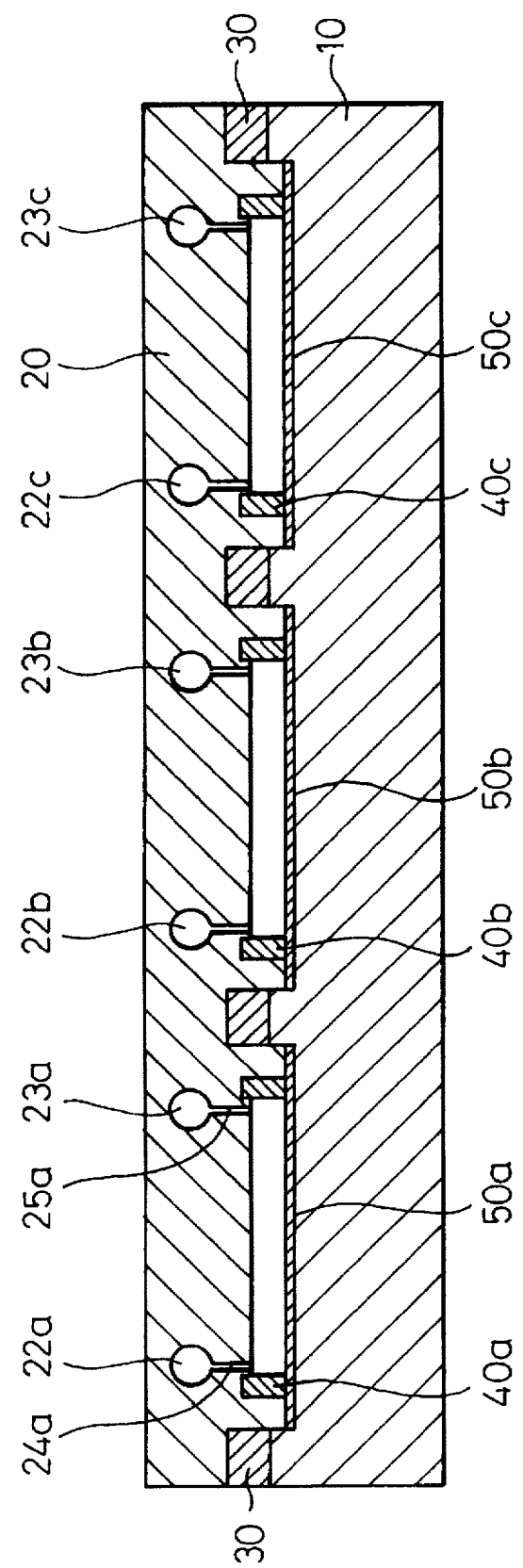
FIG. 2 is a sectional view of a flow cell.
Figure 3:
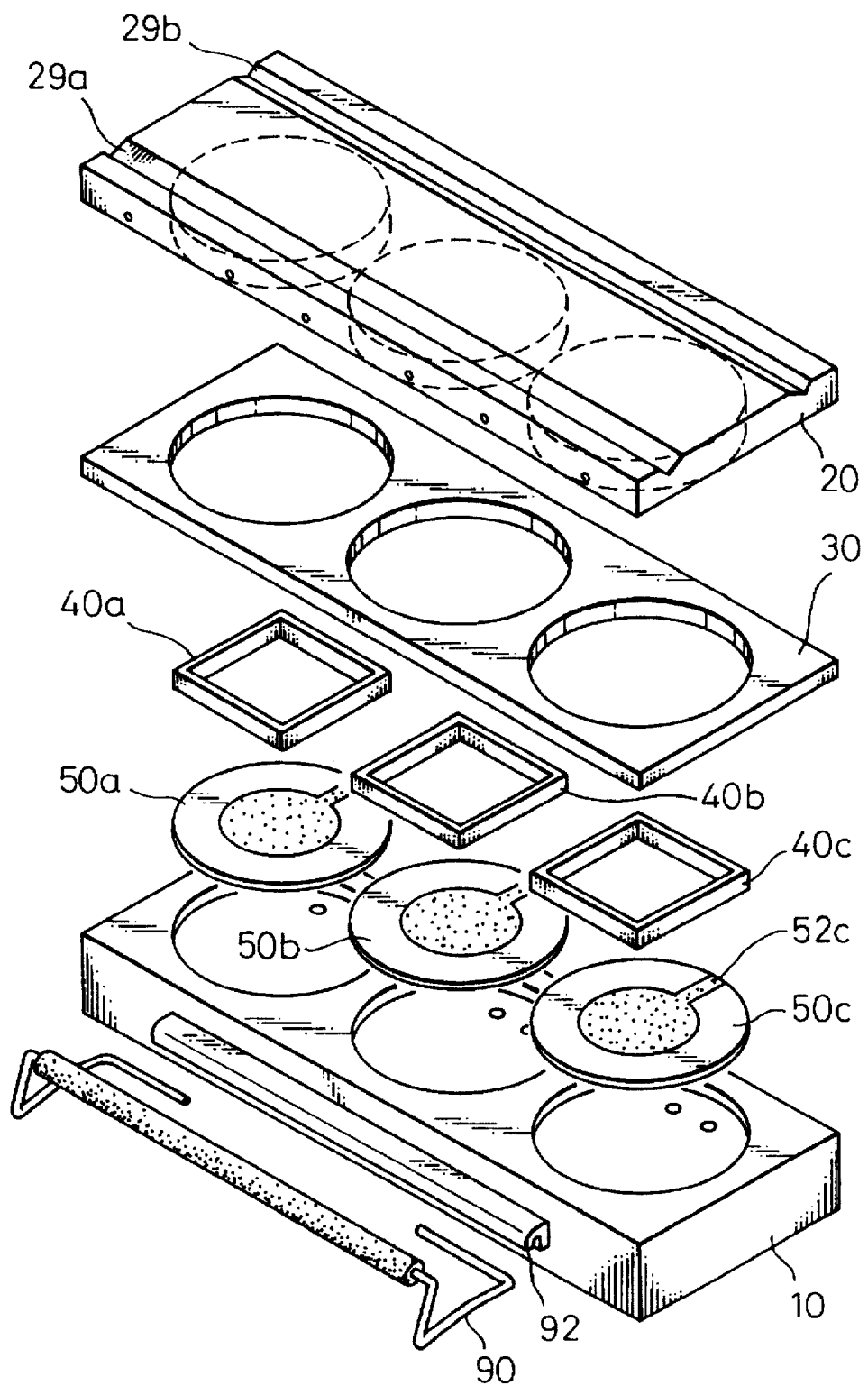
FIG. 3 is a separated view of a flow cell.

FIG. 1 is a perspective view of an embodiment of a flow cell used in a device according to the present invention, FIG. 2 is a sectional view thereof, and FIG. 3 is a separated view thereof.

Figure 4:
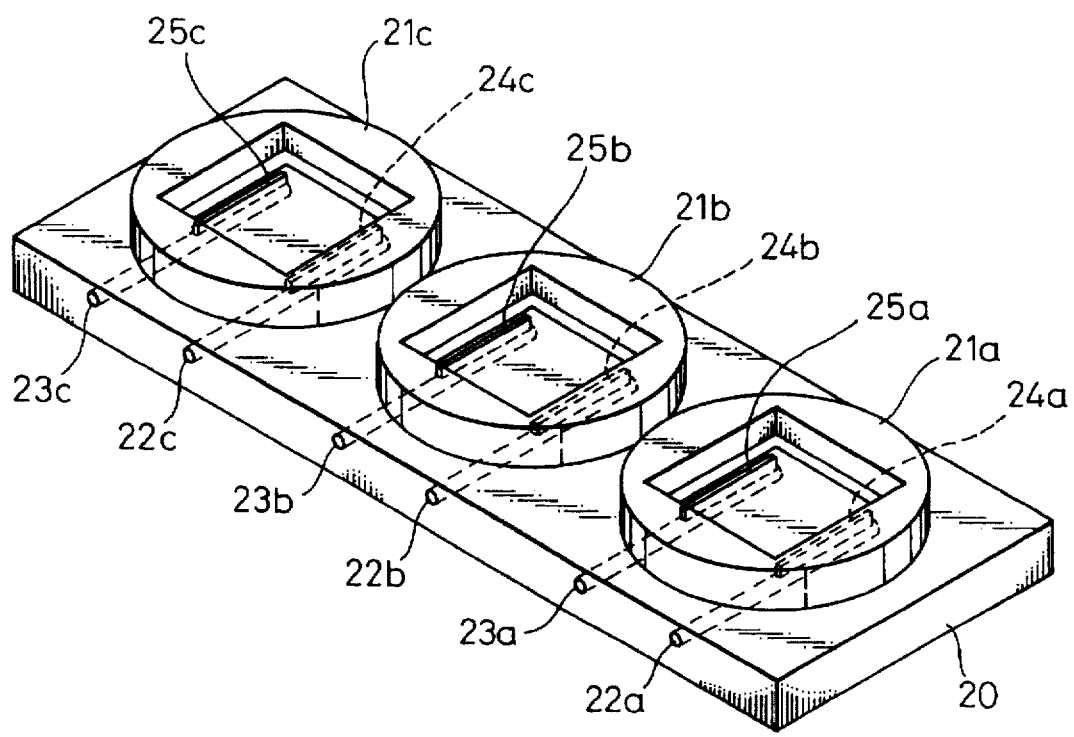
FIG. 4 is a bottom perspective view of the upper member.
Figure 5:
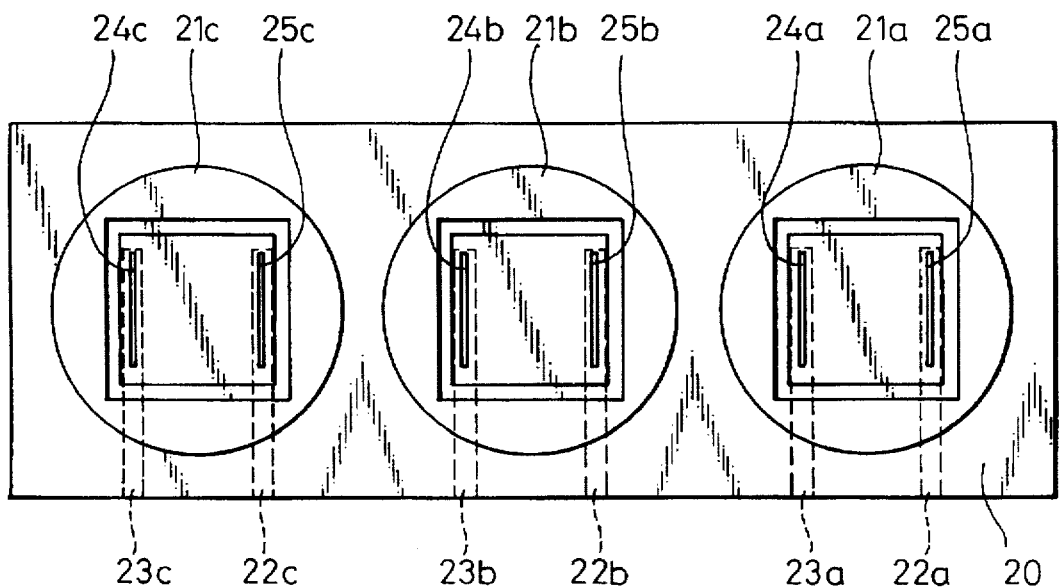
FIG. 5 is a bottom view of the upper member.

The flow cell 100 comprises a lower member 10, an upper member 20, an outer seal member 30, cell compartment seal members 40 and plate-shaped quartz oscillators 50, and it is assembled by snapping a metal clamp 90 inserted into a protrusion 92 constructed on one side of the lower member 10 into grooves 29a, 29b constructed on the top surface of the upper member 20. The upper member 20 is made or, for example, silicone-coated vinyl chloride, and as may be easily seen in the bottom perspective view in FIG. 4 and the bottom plane view in FIG. 5, collar-like raised sections 21a, 21b, 21c with a circular perimeter and having square pits therein are constructed in the center section of the bottom. Also, three pairs of holes 22, 23 are constructed on one side extending part-width, parallel to the material surface, and slits 24a, 25a, 24b, 25b, 24c, 25c are opened from the sides of the holes 22a–22c, 23a–23c toward the areas enclosed by the collar-like raised sections 21a, 21b, 21c. Tubes 61a, 62a, 61b, 62b, 61c, 62c made of a material such as Teflon (registered trademark) or silicone-coated vinyl chloride which is resistant to adhesion of blood components, are connected in the holes 22, 23 constructed on the side of the upper member 20.

Figure 6:
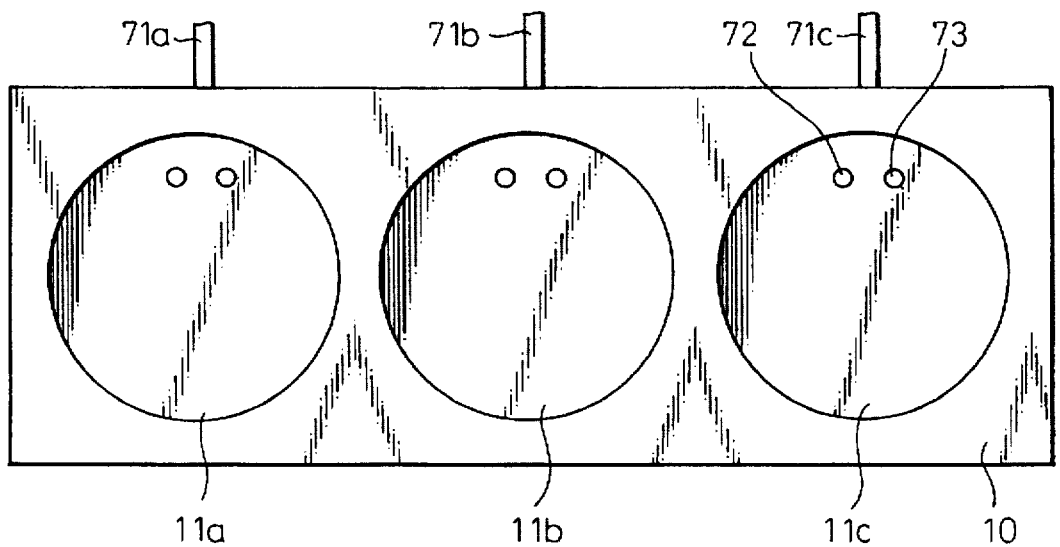
FIG. 6 is a plane view of the lower member.

The lower member 10 shown in the plane view in FIG. 6 is made of Teflon or the like, and it is provided with circular pits 11a, 11b, 11c. Cables 71a, 71b, 71c connected to an oscillator or frequency counter, not shown, are water-tightly anchored to the lower member, and electrical contacts 72, 73 connected to the conductors of the cables 71a–71c are exposed at the surface of the pits 11. Plate-shaped quartz oscillators 50a, 50b, 50c are situated in a freely detachable manner in the pits 11a–11c of the lower member 10 so that the electrodes 51a–51c are in contact with the electrical contacts 72, 73.

After cell compartment seal members 40a, 40b, 40c are fitted inside the collar-like raised sections 21a, 21b, 21c on the bottom of the upper member 20 and an outer seal member 30 is fitted around the collar-like raised sections 21a, 21b, 21c, the collar-like raised sections 21a, 21b, 21c are inserted into the pits 11a, 11b, 11c of the lower member 10, and the upper and lower members 10, 20 are clamped with the metal clamp 90 to complete assembly of the flow cell. Here, the areas defined by the plate-shaped quartz oscillators 50a–50c and the collar-like raised sections 21a–21c of the upper member 20 become the cell compartments. Blood guided through the tubes 61a–61c to each cell compartment with a pump, not shown, enters the cell compartments via the slits 24a–24c running to the holes 22a–22c formed in the upper member 20, flows in a laminar manner over the surface of the quartz oscillators 50a–50c, flows into the holes 23a–23c from the slits 25a–25c situated at the other end of each cell compartment, and is discharged via the tubes 62a–62c.

For a laminar flow of the blood, it is necessary that the cross-sectional area of the channel of the cell compartment be 50 mm$^2$ or less. In the case of this example, the measurements of the cell compartment are 0.3 mm×15 mm×15 mm (channel cross-sectional area of 4.5 mm$^2$). The fluid flows and continuous measurement of the amount of adhesion is made while the flow cell is kept immersed in a constant temperature oven at 37° C.

Figure 7:
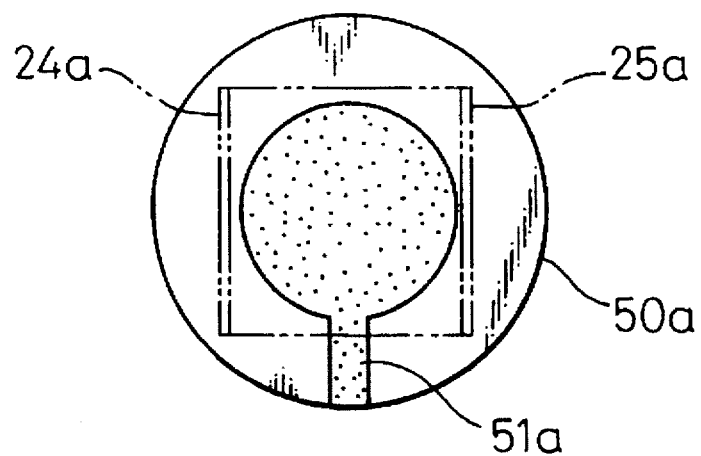
FIG. 7 is a drawing for explanation of the positional relationship between the plate-shaped crystal oscillator and the cell compartment.

From the point of view of easy handleability and measuring sensitivity, the quartz oscillators 50a–50c preferably oscillate at a basic resonance frequency of 5–10 MHz. Slits 24a–24c, 25a–25c 1 mm wide and 15 mm long for introduction and discharge of the fluid in the cell compartment in a laminar flow, are situated in the manner shown in FIG. 7 with respect to the plate-shaped quartz oscillators 50a–50c, to form the cell compartments over the plate-shaped quartz oscillators 50a–50c. The cell compartment seal members 40a–40c are silicone resin sheets 1 mm thick; and the outer seal member 30 is a silicone resin sheet 0.3 mm thick.

The measuring cells were prepared in the following manner. AT cut quartz oscillators (plate thickness: 350 μm) 50a–50c with a diameter of 2.5 cm and a basic resonance frequency of 5 MHz were immersed in a 2% aqueous solution of an alkali detergent (EXTRAN MA01, product of Merck Co.) and subjected to ultrasonic washing for 3 minutes, and then immersed in ethanol and wiped with a cloth. Commercially available polycarbonate beads (NOVALEX, product of Mitsubishi Kasei) were washed with a 2% aqueous solution of an alkali detergent (EXTRAN MA01, product of Merck Co.) and dried for an hour or longer at 100° C., and then dissolved in tetrachloroethane to a concentration of 6 wt %. This solution was used for spin coating of the plate-shaped quartz oscillators whose surfaces had been washed previously, at 1000 rpm for 10 seconds, and again at 2000 rpm for 10 seconds, and drying was effected first at 75° C. for one hour and then at 150° C. for one hour. The thickness of the polycarbonate film formed in this manner was measured with an ellipsometer and found to be 10 nm.

Figure 8:
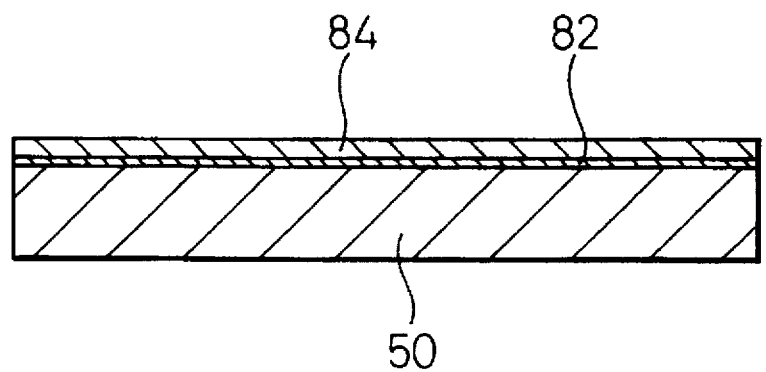
FIG. 8 is an illustrative sectional view of a measuring element.

Next, the plate-shaped quartz oscillators coated with the above-mentioned polycarbonate layer were immersed for 8 hours or longer in solutions of collagen, human fibrinogen and human von Willebrand's factor which had been adjusted to concentrations of about 20 μg/ml, and, as shown by the simplified sectional structure in FIG. 8, there were formed three different measuring elements with each of the above-mentioned proteins 84 immobilized on the polycarbonate layer 82. The film thickness of the proteins immobilized on the polycarbonate layer was about 150 nm. In these measuring elements, a resonance frequency change of 1 Hz corresponds to a mass change of 18 ng/cm$^2$.

Four different blood samples A, B, C and D were prepared. Sample A was normal blood from a healthy person, sample B was blood with impaired glycoprotein (GP)IIb/IIIa function due to anti-platelet membrane GPIIb/IIIa monoclonal antibody (Igakuseibutsu Laboratory), sample C was blood with impaired GPIb function due to anti-GPIb monoclonal antibody (Takara Shuzo), and sample D was blood with impaired GPIa/IIa function due to anti-GPIa/IIa monoclonal antibody (Immunotech).

Figure 10:
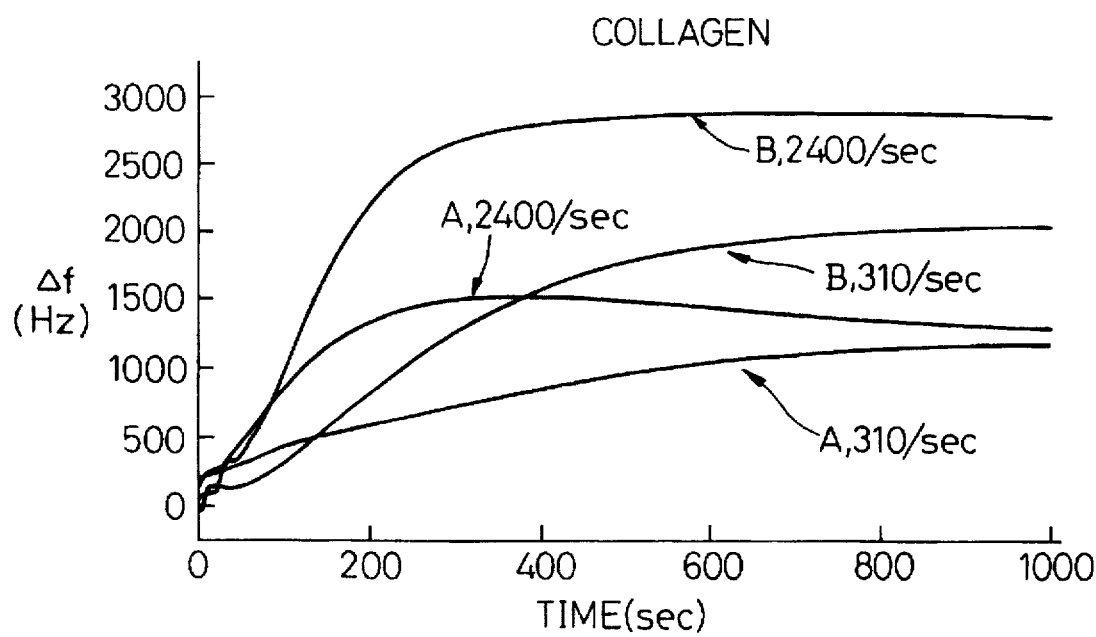
FIG. 10 is a graph showing examples of measurement of collagen.
Figure 11:
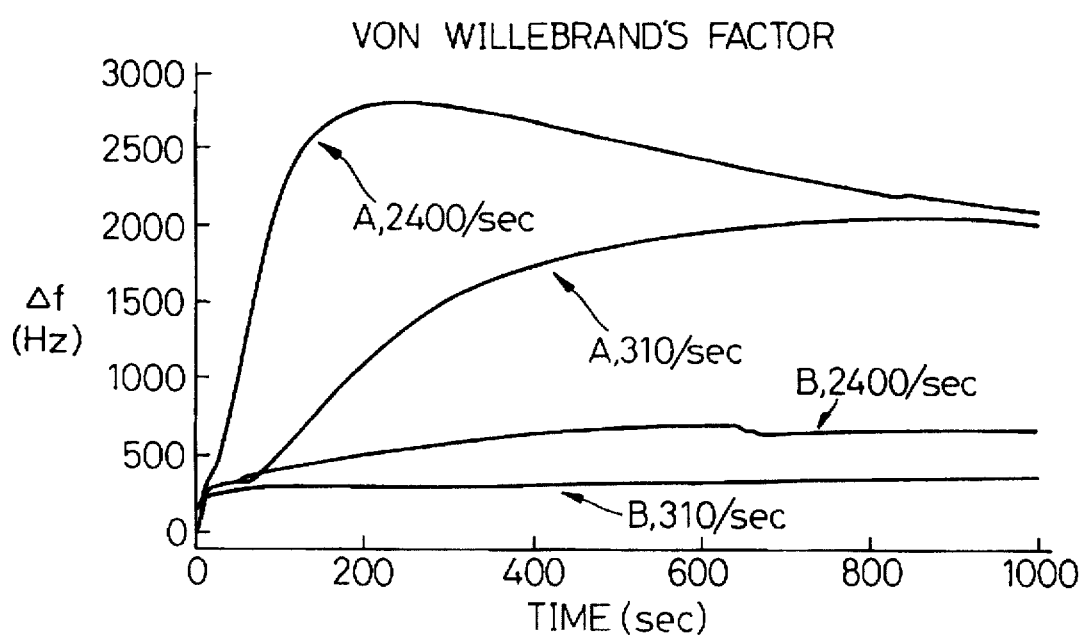
FIG. 11 is a graph showing examples of measurement of von Willebrand's factor.
Figure 12:
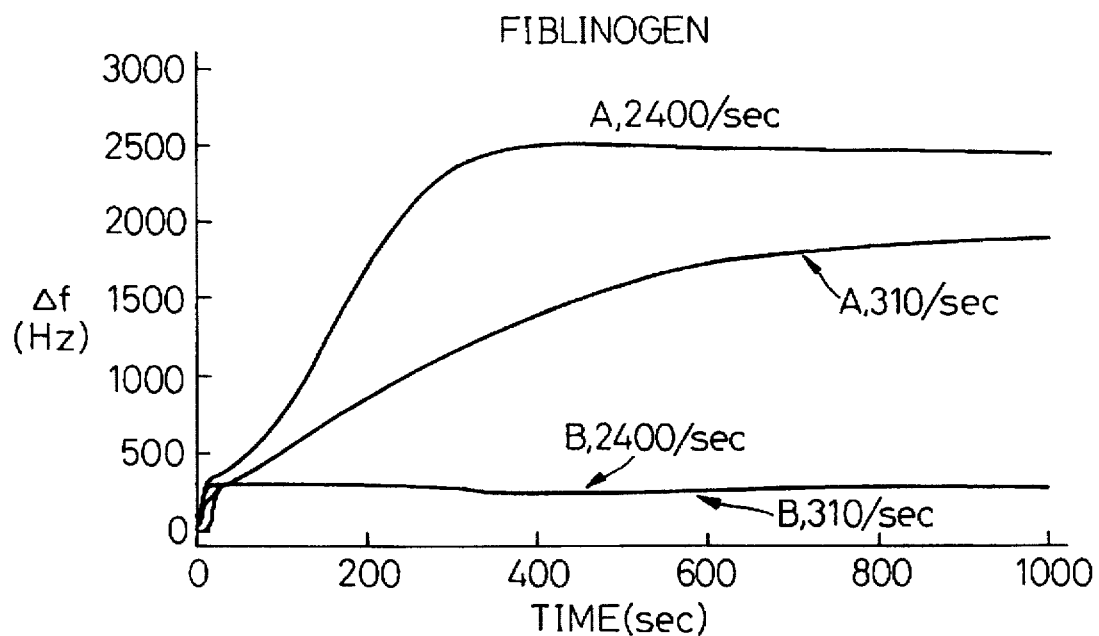
FIG. 12 is a graph showing examples of measurement of fibrinogen.

Component blood prepared by removing the platelets and leukocytes from blood taken using a P-PACK was cycled in the flow cell 100 including the measuring elements coated with the above-mentioned 3 types of proteins for about 10 minutes at a flow rate of 2400/sec, until adsorption saturation of the proteins is established. The flow cell 100 was immersed in a constant temperature bath kept at 37° C. to maintain its temperature constant. Upon cycling of the whole blood of blood samples A and B in each cell compartment, as shown in FIGS. 10 to 12, resonance frequency changes occurred in all three with sample A, whereas in the case of sample B no resonance frequency change occurred for human fibrinogen or von Willebrand's factor, while for collagen the degree of change was greater than with blood sample A. When whole blood of blood samples A and B was used for the same measurement at a flow rate of 310/sec, as shown in FIGS. 10 to 12, the same tendency was shown as with the flow rate of 2400/sec.

The same measurement was conducted using blood samples C and D. For each of these measurements, the metal clamp was removed, the flow cells were disassembled for washing with physiological saline, and the measuring element was replaced with new ones. The used plate-shaped quartz oscillators 50a, 50b, 50c of the measuring element may be immersed for 1-2 minutes in a tetrachloroethane solution and then wiped with a cloth to remove the polycarbonate layer, the protein layer and protein adhered thereonto, for later reuse.

The measurement results were evaluated in the following manner. The change $\Delta f_0$ in the resonance frequency when the normal blood sample A was cycled, and each of the changes $\Delta f$ in the resonance frequencies when blood samples B to D were cycled were taken, and the ratio $\Delta f/\Delta f_0$ was used for classification of the ratio values, wherein the case of the ratio<0.5 was indicated by (—), the case of 0.5≦the ratio<0.8 was indicated by (−), the case of 0.8≦the ratio<1.2 was indicated by (±), the case of 1.2≦the ratio<1.5 was indicated by (+), and the case of 1-5≦the ratio was indicated by (++). The evaluation was made 1000 seconds after measurement began.

In addition to whole blood, a washed blood sample prepared by taking out the erythrocytes and platelets and resuspending the same in a buffer solution was subjected to the same measurement as described above.

The results are summarized in Table 1. In the table, F stands for human fibrinogen, V for human von Willebrand's factor, and C for collagen, with the flow rate of 2400/sec indicated as "high" and 310/sec as "low".

TABLE 1

| Blood sample | Protein | Whole blood | | Washed blood | |
|---|---|---|---|---|---|
| | | high | low | high | low |
| B | F | — | — | — | — |
| | V | — | — | — | — |
| | C | ++ | ++ | ++ | ++ |
| C | F | ± | ± | — | ± |
| | V | ± | ± | — | ± |
| | C | ± | ± | — | ± |

TABLE 1-continued

| Blood sample | Protein | Whole blood | | Washed blood | |
|---|---|---|---|---|---|
| | | high | low | high | low |
| D | F | ± | ± | ± | ± |
| | V | ± | ± | ± | ± |
| | C | — | − | − | — |

From the data shown in Table 1, it may be clearly concluded that with measurement using GPIIb/IIIa-deficient whole blood, there is little or no adhesion to human fibrinogen or human von Willebrand's factor, but much adhesion to collagen. It may also be concluded that with measurement using GPIb-deficient whole blood, the adhesion to von Willebrand's factor and collagen is the same as for healthy subjects in the case of both high and low flow rates, while with measurement using GPIb-deficient washed blood there is a notable decrease in the adhesion only in the case of a high flow rate. Furthermore, it may be concluded that with measurement using GPIa/IIa-deficient blood, the adhesion to human fibrinogen and human von Willebrand's factor is the same as for healthy subjects, while there is little adhesion to collagen.

GPIIb/IIIa deficiency is associated with thrombocytasthenia, GPIb deficiency with Bernard-Soulier syndrome, and GPIa/IIa deficiency with GPIa/IIa deficiency syndrome, and therefore the use of the method according to the present invention makes it possible to perform simple diagnoses of these blood diseases.

Figure 9:
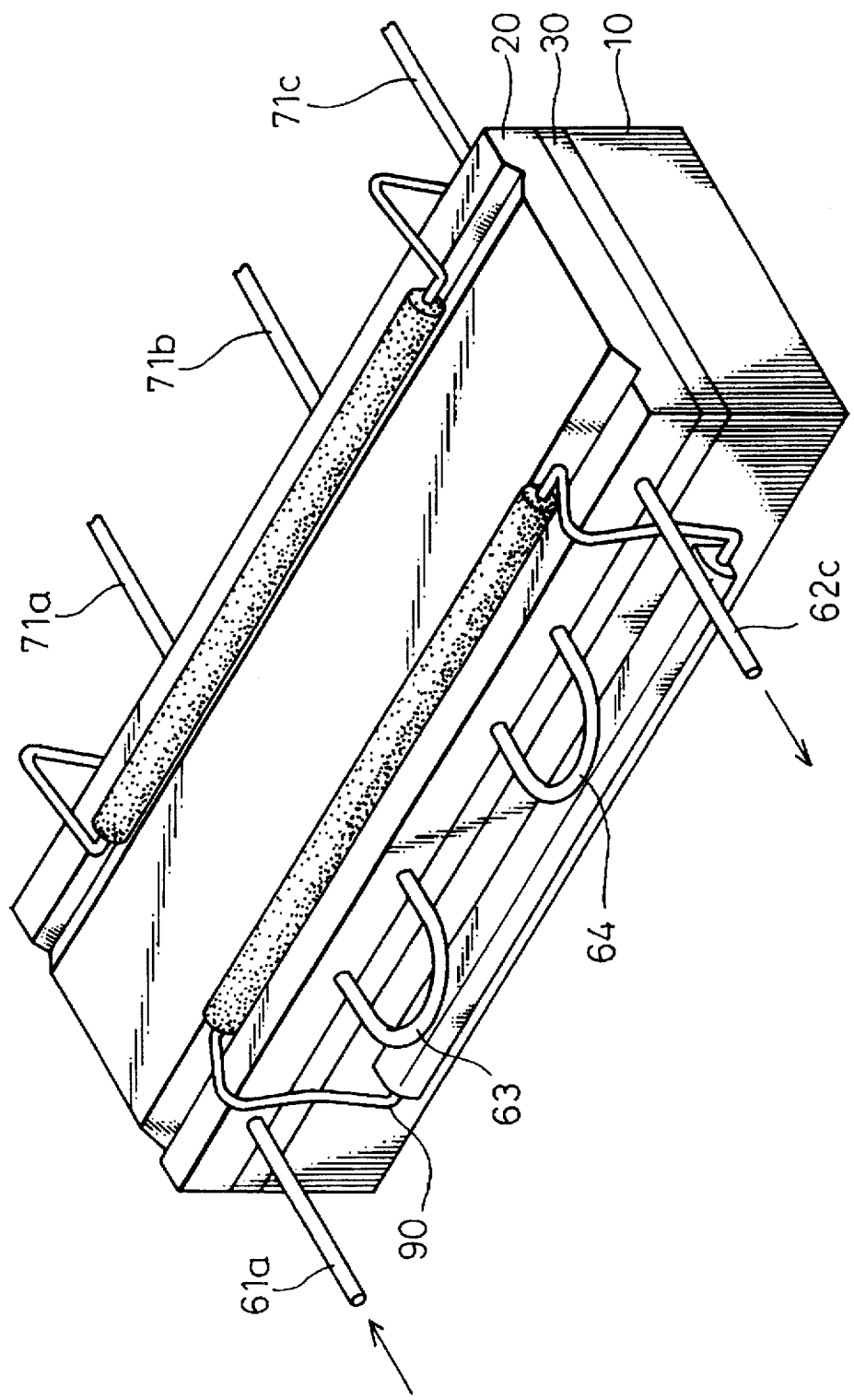
FIG. 9 is a drawing for explanation of an alternative method of connecting the tubes to the flow cell.

In this example, the blood samples were supplied in a parallel manner to the three cell compartments of the flow cell 100 via the tubes 61a–c. However, as shown in FIG. 9, the exit hole 23a and entrance hole 22b may be connected by a tube 63 and the exit hole 23b and entrance hole 22c may be connected by a tube 64 to use the cell compartments in serial connection. This case has the advantage of requiring only a single pump for transporting the blood samples to the flow cell 100.

Example 2

Blood samples A and E were prepared and measured using the same device as in Example 1. The blood sample A was normal blood from a healthy person, and the blood sample E was a blood sample lacking pachychromatie granules in the platelets. That is, blood sample E had no liberation of pachychromatic granules from the platelets, and after the initial activation the secondary aggregation reaction either did not occur or was very difficult.

Component blood prepared by removing the platelets and leukocytes from blood using a P-PACK was cycled in the flow cell which included three measuring elements coated with the above-mentioned human fibrinogen, collagen and human von Willebrand's factor respectively for about 10 minutes at a flow rate of 2400/sec, until adsorption saturation of the proteins was established. The flow cell was immersed in a constant temperature bath kept at 37° C. to maintain its temperature constant. Upon cycling of the whole blood of blood sample E in each cell compartment, the same resonance frequency changes occurred for sample E with all three proteins as with sample A.

Figure 13:
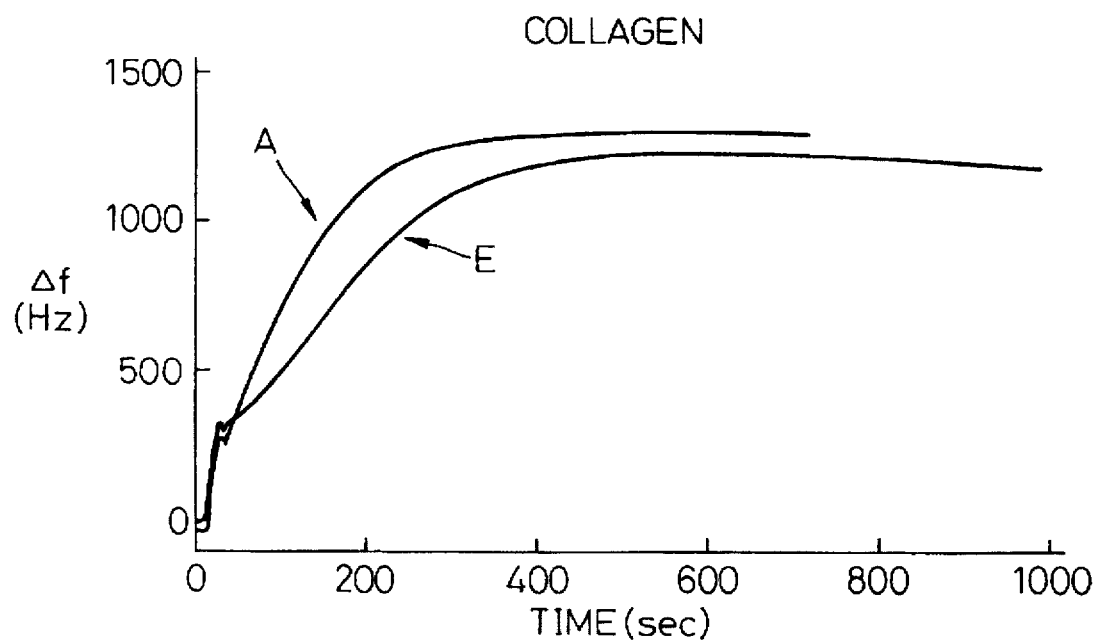
FIG. 13 is a graph showing further examples of measurement of collagen.

However, as shown in the graph in FIG. 13, the rise in the adhesion rate decreased with blood sample E. As shown in FIG. 14, this may be clearly detected by differentiating the changes in resonance frequency with a differential operator circuit.

In other words, the differential waveform of the resonance frequency change may be compared to the one of the healthy blood to detect the dysfunction of secondary coagulation. The secondary coagulation which follows the initial binding of the blood components has a strict correlation with pachychromatic granule deficiency syndrome (Hermansky-Pudlak syndrome), and using the method of the present invention it is possible to easily diagnose this syndrome.

Example 3

Blood samples F and G were prepared and measured using the same device as in Example 1. However, only one measuring cell was used which was coated with human P-selectin.

Blood sample F was a component blood prepared by removing the leukocytes out of blood using a P-PACK from a healthy person, and blood sample G was a component blood prepared by removing the leukocytes out of blood using a P-PACK from a congenital immunodeficiency syndrome patient with dysfunction of adhesion of leukocytes to P-selectin.

A buffer solution containing the above-mentioned blood sample F with the erythrocytes and leukocytes removed was cycled for about 10 minutes at a flow rate of 2400/sec in a flow cell which included the measuring element coated with human P-selectin, and the temperature was allowed to become constant. When blood sample F was then cycled, a frequency change of 800 Hz occurred in 15 minutes. On the other hand, when blood sample G was cycled in the same manner, the frequency change in 15 minutes was about 20 Hz.

According to this example, it is possible to diagnose impairment of adhesion of leukocytes to P-selectin by cycling leukocyte component blood in a measuring cell coated with human P-selectin.

Example 4

Samples H and I were prepared and measured using the same device as in Example 1. However, only one measuring element was used which was coated with human fibrinogen.

Blood sample H was a component blood prepared by removing the erythrocytes and platelets out of blood taken from a healthy person using a P-PACK, and blood sample I was a component blood prepared by removing the erythrocytes and platelets out of blood taken using a P-PACK from a sickle cell patient with reduced erythrocyte deformability.

A buffer solution containing the above-mentioned blood sample H with the erythrocytes and leukocytes removed was cycled for about 10 minutes at a flow rate of 310/sec in a flow cell which included the measuring element coated with human fibrinogen, and the temperature was allowed to become constant. When blood sample H was then cycled, a frequency change of 800 Hz occurred in 15 minutes. On the other hand, when blood sample I was cycled in the same manner, the frequency change in 15 minutes was about 2000 Hz. In other words, although there was no abnormality in the platelet function of sample I, the adhesion of platelets was clearly augmented by the reduced deformability of the erythrocytes.

Thus, it is possible to determine reduction in erythrocyte deformability by cycling component blood containing erythrocytes and leukocytes using a measuring element coated with human fibrinogen.

Example 5

Samples J and K were prepared and measured using the same device as in Example 1. Blood sample J was a blood taken using a P-PACK from a congenital fibrinogen deficiency syndrome patient lacking fibrinogen which is a protein normally present in the blood, and blood sample K was a blood taken using a P-PACK from a congenital von Willebrand's factor deficiency syndrome patient lacking von Willebrand's factor which is also a protein normally present in the blood.

Whole blood of samples J and K were cycled in flow cells at flow rates of 2400/sec (high) and 310/sec (low), and the results of evaluation based on the same criteria as in Example 1 are shown in Table 2.

TABLE 2

| Blood sample | Protein | Whole blood | |
| --- | --- | --- | --- |
| | | high | low |
| J | F | ± | ± |
| | V | ± | — |
| | C | ± | ± |
| K | F | — | ± |
| | V | ± | ± |
| | C | — | ± |

As is clear from Table 2, deficiency of fibrinogen in the blood may be determined by low adhesion to von Willebrand's factor at a low flow rate. On the other hand, deficiency of von Willebrand's factor in the blood may be determined by low adhesion to fibrinogen and collagen at a high shear rate.

Example 6

A material prepared by casting a commercially available polycarbonate in solution and a material prepared by further immobilizing human fibrinogen on the polycarbonate were attached to AT cut crystal oscillators each with a diameter of 2.5 cm and a basic resonance frequency of 5 MHz. A flow cell was fitted over each material. Component blood prepared by removing the erythrocytes and leukocytes from heparinized blood was circulated at a shear rate of 350 sec$^{-1}$ for about 10 minutes until the temperature stabilized and the protein adhesion reached saturation. Next, the antithrombogenic agent prostaglandin E1 was added to whole blood to a final concentration of 10 µM, and upon circulation there was no change in the frequency with either the polycarbonate material or the polycarbonate and fibrinogen material. However, when blood to which the antithrombogenic agent prostaglandin E1 was not added was circulated, after 15 minutes frequency changes of about 1000 Hz with the polycarbonate material and about 2000 Hz with the polycarbonate and fibrinogen material were observed.

Thus, by using this measuring device it was possible to confirm the effect of the anti-thrombogenic agent prostaglandin E1.

According to the present invention, it is possible to detect blood dysfunction sites in a quick and reliable manner using a simple method.

We claim:

1. A method for analyzing a whole blood sample, for the presence or absence of a blood abnormality comprising the steps of:
   cycling a whole blood sample from a test subject as a laminar flow having a flow rate approximating a human blood flow rate in a flow cell which comprises a measuring element comprising at least one quartz plate-shaped oscillator having a protein outer layer, said protein outer layer being operative to attach thereto a blood component specific for said protein;

measuring the amount of adhesion of blood components present in said blood sample on said protein layer based on the resonance frequency of said measuring element;

comparing the amount of adhesion to a standard value corresponding to the amount of adhesion of blood components occurring when blood from a healthy subject is cycled through said flow cell; and correlating any difference in the amount of adhesion with the presence or absence of a blood abnormality in the test subject.

2. A method according to claim 1 wherein said measuring element comprises multiple plate-shaped oscillators, each of which is coated with a different protein, and wherein adhesion of said blood components in the blood sample of the test subject to said different proteins is compared with the adhesion of blood components from a healthy subject to said different proteins from a healthy individual.

3. A method for analyzing a whole blood sample according to claim 1, wherein said protein outer layer comprises human fibrinogen, human von Willebrand's factor, collagen or human P-selectin.

4. A method for analyzing a whole blood sample for the presence or absence of a blood abnormality comprising the steps of:

cycling a whole blood sample from a test subject as a laminar flow having a flow rate approximating a human blood flow rate in a flow cell comprising a plurality of plate-shaped quartz oscillator measuring elements prepared by coating a different protein layer on the surface of each of said plurality of plate-shaped quartz oscillator measuring elements, each protein layer being operative to attach thereto a blood component specific for said protein;

measuring the amount of adhesion of blood components present in the blood sample on the protein layer of each of said plurality of measuring elements based on a change in resonance frequency of said measuring elements;

comparing the amount of adhesion to a standard value corresponding to the amount of adhesion of blood components occurring when blood from a healthy subject is cycled through said flow cell; and correlating any difference in the amount of adhesion with the presence or absence of a blood abnormality in the test subject.

5. A method according to claim 4, wherein said protein layers comprise human fibrinogen, human von Willebrand's factor and collagen.

6. A method for analyzing a whole blood sample, for the presence or absence of a blood abnormality comprising the steps of:

(A) cycling a whole blood sample from a test subject as a laminar flow having a flow rate approximating a human blood flow rate in a flow cell comprising a measuring element comprising a plate-shaped quartz oscillator having a protein outer layer, said protein layer being operative to attach thereto a blood component specific for said protein;

(B) measuring the rate of adhesion of blood components present in said blood sample on said protein layer by determining a change in resonance frequency of said measuring element;

(C) comparing the change in resonance frequency obtained in step (B) with a standard value corresponding to the rate of adhesion of blood components occurring when blood from a healthy subject is cycled through said flow cell; and (D) correlating any difference in the rates of adhesion with the presence or absence of a blood abnormality in the test subject.

7. A device for analyzing a blood sample, comprising a flow cell which comprises a plurality of measuring elements each of which is prepared by plating a surface of a plate-shaped quartz oscillator with a different protein layer, means for flowing a blood sample through said flow cell at a rate approximating a human blood flow rate, means for measuring a change in resonance frequencies of said measuring elements, a plurality of serially linked means for measuring values of changes in resonance frequencies; and means for comparing the values of the changes in resonance frequencies with a prestored standard value.

8. A device according to claim 7, further comprising means for outputting results of the comparison of changes in resonance frequencies.

9. A device according to claim 7, further comprising means for differentiating the values of the changes in resonance frequencies.

10. A device according to claim 7, wherein said plurality of measuring elements are a plate-shaped quartz oscillator coated with human fibrinogen, a plate-shaped quartz oscillator coated with human von Willebrand's factor, and a plate-shaped quartz oscillator coated with collagen.

11. A method for determining the anti-thrombogenic effect of an anti-thrombogenic agent against thrombus formation caused by materials having high coagulating properties and biological tissue, comprising the steps of:

forming a layer of a material having high coagulating properties or biological tissue on a surface of a quartz oscillator comprising a portion of a wall of a flow cell, said material or biological tissue being operative to attach thereto a blood component specific for said material or biological tissue, circulating whole blood containing an anti-thrombogenic agent through said flow cell at a flow rate approximating a human blood flow rate, and detecting the amount or rate of adhesion of blood components on said layer of the material or biological tissue under said blood flow rate based on a change in resonance frequency of said quartz oscillator.

* * * * *

UNITED STATES PATENT AND TRADEMARK OFFICE
CERTIFICATE OF CORRECTION

PATENT NO. : 5,728,583
DATED : March 17, 1998
INVENTOR(S) : Keiko Kawakami, et. al.

It is certified that error appears in the above-identified patent and that said Letters Patent is hereby corrected as shown below:

| Column | Line | |
|---|---|---|
| 1 | 5 | After "1994" insert --,--. |
| 5 | 36 | Change "or," to --of,--. |
| 6 | 32 | After "thick" change ";" to --,--. |
| 7 | 45 | Change "1-5≤the" to --1.5≤ the--. |
| 8 | 46 | Change "pachychromatie" to --pachychromatic--. |
| 10 | 60 | After "sample" delete ",". |
| 10 | 61 | After "abnormality" insert --,--. |
| 11 | 20 | After "proteins" delete "from a healthy individual". |
| 11 | 53 | After "sample" delete ",". |
| 11 | 54 | After "abnormality" insert --,--. |

Signed and Sealed this

Twenty-second Day of September, 1998

Attest:

BRUCE LEHMAN

*Attesting Officer*  *Commissioner of Patents and Trademarks*